United States Patent [19]

Kromer et al.

[11] Patent Number: 4,612,106
[45] Date of Patent: Sep. 16, 1986

[54] COOLING SYSTEM FOR A SLAB GEL ELECTROPHORESIS APPARATUS

[76] Inventors: Heiner M. Kromer, 115 E. 87th St., Apt. 35C, New York, N.Y. 10028; Daniel November, 82-11 Greenfell St., Ken Gardens, Queens, N.Y. 11415

[21] Appl. No.: 685,798

[22] Filed: Dec. 24, 1984

[51] Int. Cl.⁴ ............................................. G01N 27/28
[52] U.S. Cl. ............................. 204/299 R; 204/182.8
[58] Field of Search ............ 204/180 G, 299 R, 182.8, 204/301

[56] References Cited

U.S. PATENT DOCUMENTS

| | | | |
|---|---|---|---|
| 3,374,166 | 3/1968 | Raymond | 204/180 G |
| 3,506,554 | 4/1970 | Broome | 204/180 G |
| 3,719,580 | 3/1973 | Roberts et al. | 204/180 G |
| 4,101,401 | 7/1978 | Hoefer | 204/180 G |

FOREIGN PATENT DOCUMENTS 496045 3/1976 U.S.S.R. .

OTHER PUBLICATIONS

Kern, D. Q., Process Heat Transfer, McGraw-Hill Book Company Inc., New York, pp. 472–474 (1950).

Primary Examiner—Niebling, John F.
Assistant Examiner—B. J. Boggs, Jr.
Attorney, Agent, or Firm—M. K. Silverman

[57] ABSTRACT

Disclosed herein is a gel slab electrophoresis device having novel temperature and heat control capability. The electrophoresis device includes a sample unit having a pair of transversely-spaced first and second plates containing a gel cast, these plates having open top and bottom slots spaced therebetween. An integral part of the apparatus is a heat sink which is in thermal communication with the sample unit, the heat sink constituting a pneumatic circuit for both heat distribution and removal to and from the gel cast. There is also provided upper and lower solution chambers, both filled with conductive solutions, and both in fluid communication with the respective top and bottom portions of the gel. The apparatus also includes an arrangement for applying an electrical potential between the upper and lower solution chambers and, thereby, across the entire vertical length of the gel. Additionally provided is a refrigeration sub-system, the output of which is heat exchanged into the pneumatic circuit.

8 Claims, 6 Drawing Figures

COOLING SYSTEM FOR A SLAB GEL ELECTROPHORESIS APPARATUS

BACKGROUND OF THE INVENTION

The present invention relates to a cooling apparatus for performing gel slab electrophoresis.

A longstanding problem in the usage of electrophoresis apparatus has been the danger of electrical shock from high voltages required in prior art electrophoresis systems and, as well, degradation in the test results caused by unwanted excursions of both heat and temperature.

Most cooling arrangements used with electrophoresis systems have required the usage of water or other liquid coolant. In addition to difficulty in maintaining heat and temperature control in such systems, the danger of electrical shock, because of the use of a liquid coolant, has always been of concern to manufacturers and users of electrophoresis equipment.

The prior art has exhibited little in the way of the use of pneumatic means to effectuate cooling and temperature control of electrophoretic devices. To the knowledge of the Applicants, the only pertinent art comprises U. S. Pat. Nos. 3,499,833; 3,867,271; 4,234,400; and 4,310,408. None of the arrangements shown in these patents are useful for the generalized heat and temperature control capability provided by the invention disclosed herein.

The instant invention is believed to be properly classified in U. S. Class 204, Subclass 299R.

SUMMARY OF THE INVENTION

The invention comprises an electrophoresis device having temperature and heat control capability. Included therein is a specimen unit having a pair of transversely-spaced first and second plates containing a gel cast, said plates having open top and bottom slots spaced therebetween. An integral part of the apparatus is the heat sink which is in thermal communication with a sample unit. The heat sink comprises a pneumatic circuit for both heat distribution and removal from the gel cast. There is also provided upper and lower solution chambers, both filled with conductive solutions and in fluid communication with the respective top and bottom portions of the gel. The inventive apparatus also includes an arrangement for applying an electrical potential between the upper and lower solution chambers and, thereby, across the entire vertical length of the gel. An important feature of the inventive system resides in a refrigeration sub-system, the output of which is heat exchanged into said pneumatic circuit in order to thereby improve the cooling capability of the present temperature and heat control system.

It is an object of the present invention to provide an improved heat and temperature control means for an electrophoresis device.

It is a further object to provide a temperature control system for an electrophoresis device that will facilitate a more uniform distribution and control of heat in the test medium to thereby maximize the accuracy of the test results obtained therefrom.

It is a still further object to provide an electrophoresis device having improved safety characteristics with respect to electrical shock hazards.

The above and other objects and advantages of the present invention will become apparent in the hereinafter set forth Detailed Description of the Invention, the Drawings and the Claims appended herewith.

DETAILED DESCRIPTION OF THE INVENTION

Figure 1:
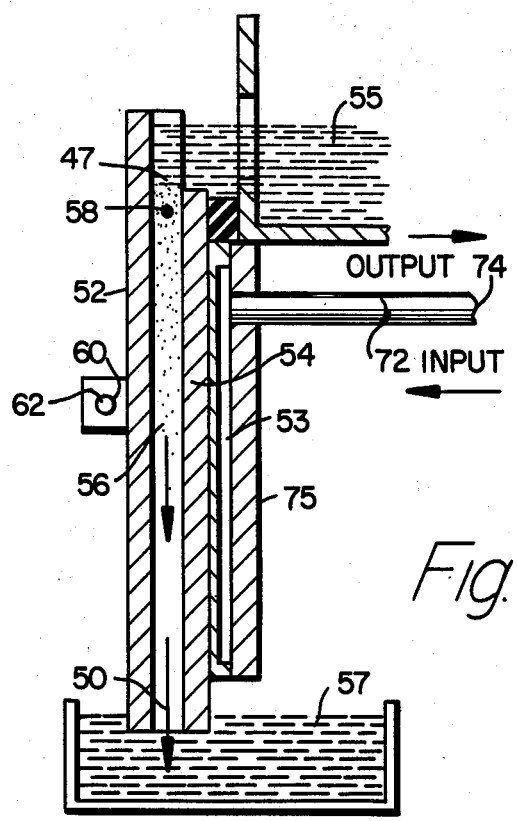
FIG. 1 is a side cross-sectional view of the electrophoresis device and cooling system.

With reference to the side cross-sectional view of FIG. 1, there is shown a sample unit of a vertical gel slab 48 electrophoresis apparatus which includes a pair of transversely-spaced first and second plates, 52 and 54 respectively, for containing a gel column 56, said plates having open top and bottom slots, 47 and 50 respectively, therebetween. Also provided is an upper solution chamber 55 filled with a first conductive solution, said solution in fluid communication with said gel 56 through said top slot 47. There is further provided a lower solution chamber 57 filled with a second conductive solution, said solution in fluid communication with said gel 56 through said bottom slot 50.

Also provided are means (not shown) for applying an electrical potential between said upper and lower solution chambers 55 and 57 and, thereby across the entire vertical length of said gel.

Figure 4:
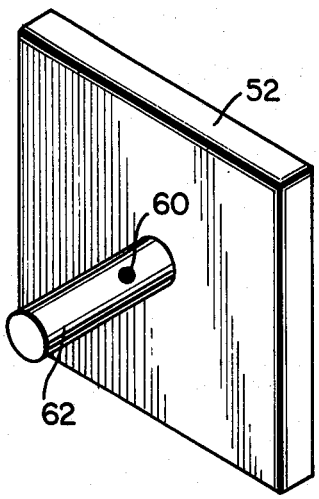
FIG. 4 is a perspective schematic view of the temperature sensor.

Also shown in FIG. 1 are the test sample 58, which is disposed at the top of the gel column 56; and thermistor 60, disposed upon plate 52, with its protective housing 62. See also FIG. 4.

In thermal communication with plate 54 is a heat sink 53, said heat sink comprising means for heat distribution and removal through and from said gel. The heat sink 53 is in the character of a pneumatic circuit comprising serpentine piping 73 (see FIGS. 2 and 6) defining a portion of a closed-loop, temperature control, air circulating system, further providing for continuous inflow and outflow of liquid, air or another gaseous fluid through said fluid jacket.

Figure 2:
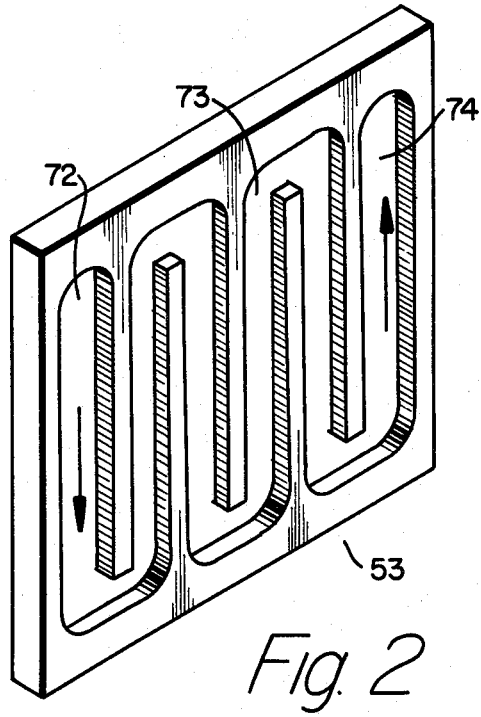
FIG. 2 is a perspective schematic view of the pneumatic cooling coils which are in thermal communication with the test medium.
Figure 3:
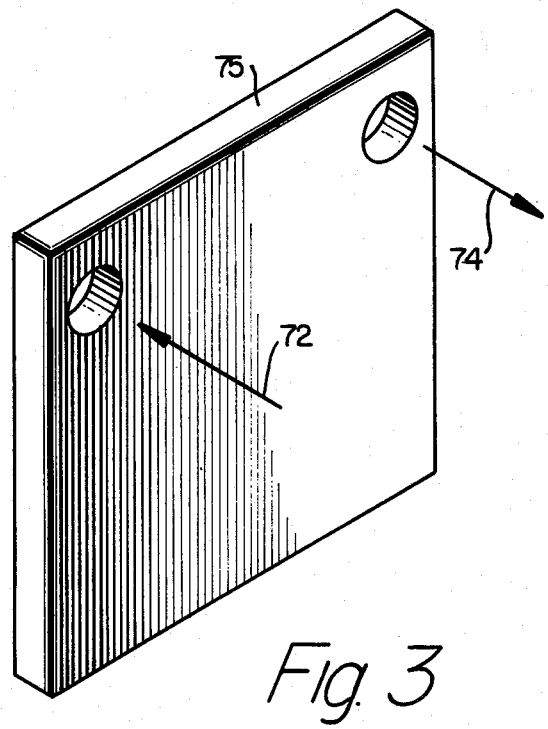
FIG. 3 is a perspective schematic view of the protective cover for the thermal jacket.
Figure 6:
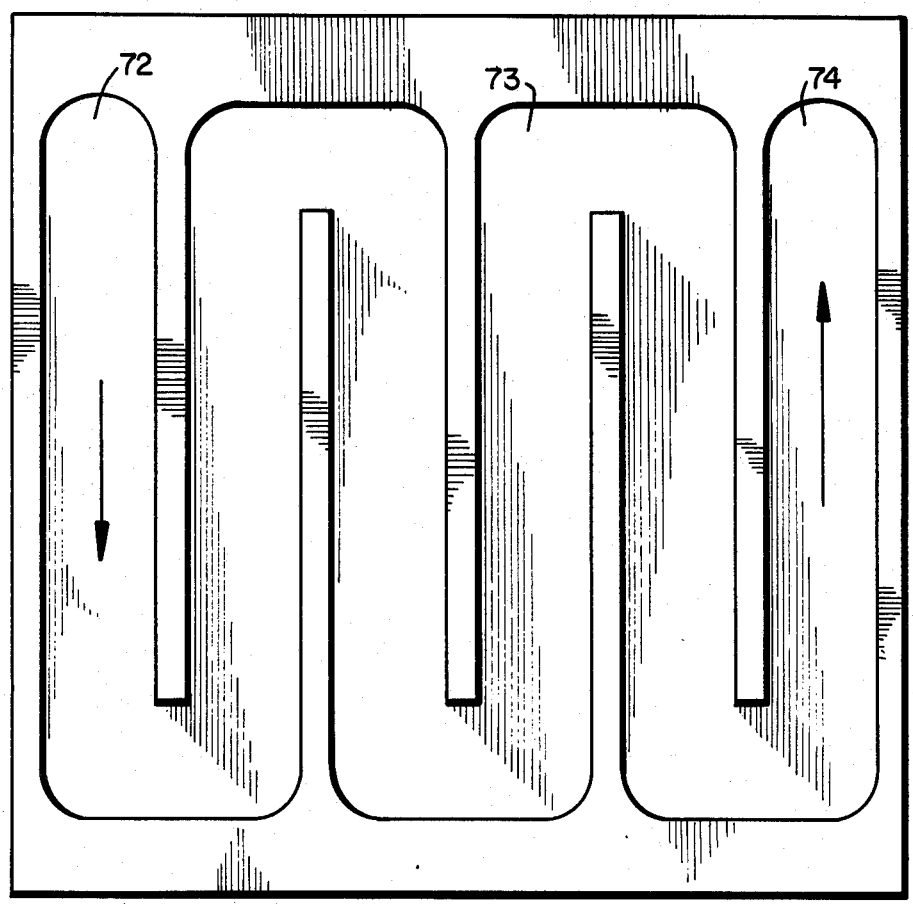
FIG. 6 is a longitudinal cross-sectional view of the cooling coil.

With reference to the perspective view of FIG. 2 and the cross-sectional view of FIG. 6, the heat sink 53 is seen to include an air input 72 and an air output 74. These inputs and outputs pass through a protective cover 75 which is more fully shown in FIG. 3

Figure 5:
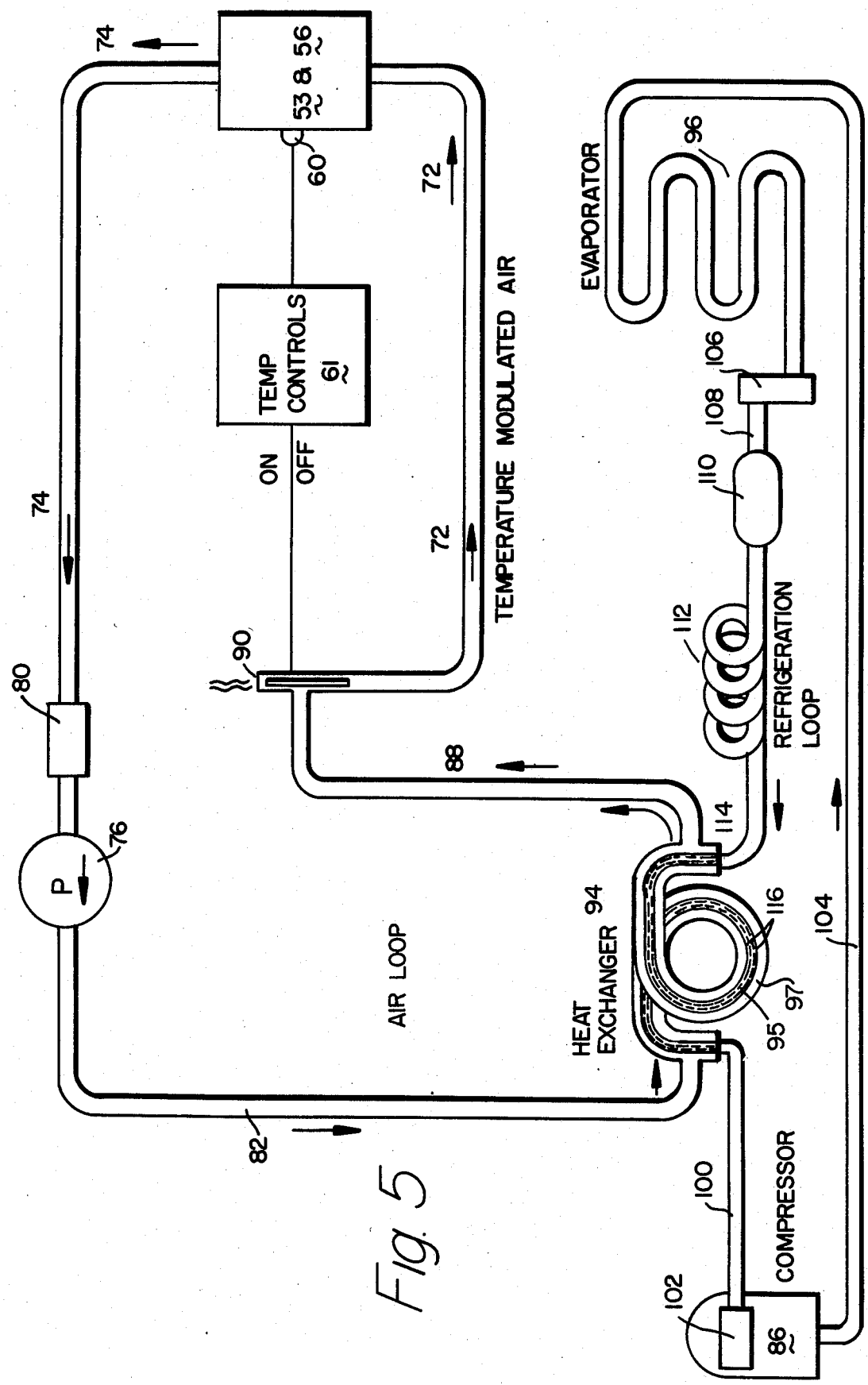
FIG. 5 is a system diagram of the heating and cooling means.

In FIG. 5 is shown the preferred embodiment of the closed-loop air circulating, cooling and heating system. More particularly, at the lower portion of FIG. 5 shown is the "refrigeration loop" of the system which includes an exchanger 94 (later described in further detail), a suction line 100, a service valve 102, and a compressor 86. The compressor is a standard ⅓ horsepower refrigeration-type unit. From the compressor, the working substance of the refrigeration sub-system passes through return line 104 and into evaporator 96. Therefrom, the gaseous output of evaporator 96 passes through service valve 106, service valve output line 108, filter/dryer 110, and into capillary restrictor coil 112 which performs a classical throttling valve function in a refrigeration system. The output of restrictor coil 112 passes through output junction 114 and through the axial center 95 of heat exchanger 94. Thereby, refrigerated gaseous working fluid passes through the longitudinal center portion 95 of the heat exchanger 94. The output thereof enters suction line 100 and is pulled into compressor 86 from which the refrigeration loop is repeated.

The air loop of the present temperature control system includes the pneumatic circuit input 72 to the slab gel 48, the slab gel structure (see FIGS. 1 and 2), the pneumatic circuit output 74 from the slab gel, where the pneumatic circuit enters a vapor filter-trap 80 and, therefrom, enters air pump 76. The output of the air pump passes through tube 82 and, therefrom into the outer annulus 97 of heat exchanger 94. It is noted that said outer annulus channel of the pneumatic circuit parallels line 116. That is, the chilled working substance passing through longitudinal channel 95 of the heat exchanger will be in thermal communication with the air (or other fluid) passing through the annular air line 97 of heat exchanger 94. The interface wall 116 must of course comprise a thermally conductive material.

From exchanger 94, the pneumatic circuit proceeds through channel 88 and into heating element 90. The heating element is activated only upon command from temperature electronics means 61 which, in turn, is controlled by thermostat means 60 which is in thermal contact with first plate 52 of the gel slab 48. See FIG. 4.

After heating element 90, the pneumatic circuit passes into the heat sink input 72, the result being temperature modulated air, resultant from the selective heating action from heating element 90 and the continuous cooling action of the refrigeration loop as interfaced with the pneumatic circuit through wall 116 of heat exchanger 94.

The entire system may be connected to any one of various electrophoresis devices 48 in order to form a pneumatic air jacket about the electrophoresis device 40 which, responsive to thermistor 60, will selectively cool and heat the sample unit in order to retain the desired thermal characteristic within the test sample.

Forced air is circulated by means of flexible hoses which can be attached or detached at will to any one of a number of electrophoresis devices.

The temperature of the circulating air is maintained by resetting the temperature control 61 which causes the heating element 90 to activate as required. The cooling unit works continuously while the heater bucks against it as needed. Temperature is read and controlled by the insulated thermistor 60.

The air flow is in the neighborhood of four cubic feet per minute through the closed loop. It is to be appreciated that a number of gaseous substances may be used as alternative to air.

The effective temperature control range of the present system is between 4° and 40° C. It has been found that this system will facilitate precise temperature control of the gel 56 without the hazard of electrical shock that is present in water-circulating type systems. Complete electrical protection of the user's system is obtained by the natural insulative qualities of circulating air within a vinyl tubing arrangement.

While there has been shown and described the preferred embodiment of the present invention, it will be understood that the invention may be embodied otherwise as herein illustrated and described; and that within said embodiments, certain changes in the detail, construction, form and arrangement of the parts, may be made without departing with the underlying ideas and principles of this invention within the scope of the appended claims.

Having thus described our invention, what we claim as new, useful and non-obvious and, accordingly, secure by letters patent of the United States is:

1. A gel slab electrophoresis apparatus, comprising:
   (a) a sample unit including a pair of transversely-spaced first and second plates containing a gel, said first and second plates having open top and bottom slots therebetween;
   (b) an upper solution chamber filled with a first conductive solution, said first solution in fluid communication with said gel through said top slot;
   (c) a lower solution chamber filled with a second conductive solution, said second solution in fluid communication with said gel through said bottom slot;
   (d) means for applying an electrical potential between said upper and lower solution chambers and, thereby, across the vertical length of said contained gel; and
   (e) a heat sink in substantial thermal communication with said sample unit, said heat sink comprising means for continuously controlling the temperature of said sample unit, the controlling means comprising a closed-loop pneumatic circuit disposed in thermal communication with said sample unit, the temperature controlling means including means for continuous inflow and outflow of air through said pneumatic circuit, said closed-loop pneumatic circuit including air refrigeration means and heating means for respectively cooling and heating the region of thermal communication between said pneumatic circuit and said sample unit, responsive to temperature monitoring means disposed upon one of said plates of said sample unit, said controlling means further comprising thermostat means for regulation of the "on" period of said heating means relative to the operation of said cooling means.

2. The apparatus as recited in claim 1 in which said pneumatic circuit further comprises a serpentine coil in the region of thermal communication with said sample unit.

3. The apparatus as recited in claim 1 in which said cooling means comprises means for continuous operation thereof.

4. The apparatus as recited in claim 3 in which said pneumatic circuit further comprises vinyl tubing as an air containment and circulation means.

5. The apparatus as recited in claim 3 in which said air refrigeration means comprises a heat exchange coil disposed between an output of the evaporator of said refrigeration means and an input to a compressor of said refrigeration means, said heat exchanger defining a thermal interface between the air flow through said pneumatic circuit and the refrigerant flow through said refrigeration means.

6. The apparatus as recited in claim 5 in which said thermal interface comprises a common heat conducting wall between two annular flow paths, one of said annular flow paths having said refrigerant flow therethrough, and the other path having said air flow therethrough.

7. The apparatus as recited in claim 1 in which said air refrigeration means comprises a heat exchange coil disposed between an output of the evaporator of said refrigeration means and an input to a compressor of said refrigeration means, said heat exchanger defining a thermal interface between the air flow through said pneumatic circuit and the refrigerant flow through said refrigeration means.

8. The apparatus as recited in claim 7 in which said thermal interface comprises a common heat conducting wall between two annular flow paths, one of said annular flow paths having said refrigerant flow therethrough, and the other path having said air flow therethrough.

* * * * *